United States Patent [19]

Takahashi et al.

[11] Patent Number: 5,246,906

[45] Date of Patent: Sep. 21, 1993

[54] THERMOSENSITIVE RECORDING MATERIAL

[75] Inventors: Yoshiyuki Takahashi, Kawasaki; Akiko Iwasaki, Urawa; Kunitaka Toyofuku, Sakura, all of Japan

[73] Assignee: Oji Paper Co., Ltd., Tokyo, Japan

[21] Appl. No.: 913,943

[22] Filed: Jul. 17, 1992

[30] Foreign Application Priority Data

Aug. 2, 1991 [JP] Japan .................................. 3-194318
Oct. 25, 1991 [JP] Japan .................................. 3-280053

[51] Int. Cl.$^5$ ............................................. B41M 5/30
[52] U.S. Cl. ............................... 503/209; 503/214; 503/216; 503/225
[58] Field of Search .................. 503/209, 214, 216, 225

[56] References Cited

U.S. PATENT DOCUMENTS

| 3,539,375 | 11/1979 | Baum | 117/36.2 |
| 4,531,139 | 7/1985 | Seitz | 503/225 |

FOREIGN PATENT DOCUMENTS

| 0196164A2 | 10/1986 | European Pat. Off. . |
| 43-4160 | 2/1568 | Japan . |
| 45-14039 | 5/1970 | Japan . |
| 48-27736 | 4/1973 | Japan . |
| 56-146794 | 11/1981 | Japan . |
| 58-199189 | 11/1983 | Japan . |
| 59-114096 | 6/1984 | Japan . |
| 59-167292 | 9/1984 | Japan . |
| 60-78782 | 5/1985 | Japan . |
| 60-219088 | 11/1985 | Japan . |
| 62-164579 | 7/1987 | Japan . |
| 5993387 | 5/1989 | Japan . |

OTHER PUBLICATIONS

Patent Abstracts of Japan, vol. 10, No. 176 (M-491)(2232) Jun. 20, 1986 & JP-A-61 027 287 (Ricoh Co Ltd) Feb. 6, 1986.
Patent Abstracts of Japan, vol. 5, No. 174 (M-96)(846) Nov. 10, 1981 & JP-A-56 099 695 (Ricoh K.K.) Aug. 11, 1981.

*Primary Examiner*—Pamela R. Schwartz
*Attorney, Agent, or Firm*—Armstrong, Westerman, Hattori, McLeland & Naughton

[57] ABSTRACT

A thermosensitive recording material capable of recording thereon colored images having high resistances to oily substances, plasticizers, moisture, and heat and an excellent storage persistency over a long time, comprises a thermosensitive colored image-forming layer formed on a sheet substrate and comprising a colorless dye precursor, a color developing agent, and a binder, the color developing agent comprising at least one compound of the formula (I):

$$R^1-SO_2-NHCH\underset{X}{\overset{R^2}{\underset{\|}{\diagup}}}R^3$$

wherein X is an O or S atom, $R^1$ is an unsaturated aromatic group or a substituted phenyl group having a lower alkyl or halogen atom and $R^2$ and $R^3$ are respectively a hydrogen atom, alkyl, aralkyl, substituted alkyl having an aryloxy, unsubstituted aromatic group, or substituted aromatic group having at least one substituent selected from alkyl, aryl, aralkyl, alkyloxy, alkyloxycarbonyl, aryloxycarbonyl, aralkyloxycarbonyl, and arylsulfonyl groups, and halogen atoms.

7 Claims, No Drawings

THERMOSENSITIVE RECORDING MATERIAL

BACKGROUND OF THE INVENTION

1. Field of the Invention

The present invention relates to a thermosensitive recording material on which colored images are formed by heating. More particularly, the present invention relates to a thermosensitive recording material capable of forming thereon colored images having a high resistance to fading and thus exhibiting a high persistency during storage thereof for a long time.

The thermosensitive recording material of the present invention is able to record thereon colored images exhibiting an excellent resistance to moisture, heat, oily and fatty substances, and plasticizers, and thus has a superior persistency when stored for a long time and therefore is useful as colored image-recording sheets, sheets for use in facsimiles, word processors, CRT image printers and cash dispensers, as passenger tickets, commuter passes, labels such as POS labels, cards such as prepaid cards, and as transit passes.

2. Description of the Related Arts

It is known that a conventional thermosensitive recording material comprises a supporting substrate, for example, a paper sheet, synthetic paper sheet, or plastic resin film and a thermosensitive colored image-forming layer formed on a surface of the supporting substrate and comprising an electron-donative dye precursor, for example, a leuco basic dye, an electron-acceptive color-developing agent consisting of an organic acid substance, for example, a phenol compound, and a binder. When the thermosensitive colored image-forming layer is heated imagewise, colored images are recorded thereon by a reaction of the dye precursor with the color-developing agent.

This type of thermosensitive recording material is disclosed in Japanese Examined Patent Publication Nos. 43-4,160 and 45-14,039 and Japanese Unexamined Patent Publication No. 48-27,736, and is widely employed in practice.

Namely, the thermosensitive recording material is advantageous in that colored images can be easily formed by heating alone, and the recording apparatus can be made compact and small in size, has a relatively low cost, and can be easily maintained. Therefore, the thermosensitive recording material is appreciated as a useful information-recording material for recording outputs of printers used with, for example, computers, facsimile machines, automatic ticket-vending machines, scientific measurement recorders, and CRT medical measurement recorders.

Nevertheless, the conventional dye-forming type thermosensitive recording materials in which the thermosensitive colored image-forming layer comprises a conventional color-developing agent together with the dye precursor and the binder is disadvantageous in that the resultant colored images fade with the lapse of time. Presumably due to a reversible reaction of the dye recursor with the color-developing agent. This fading of the colored images is accelerated by exposure to light, high temperatures, and high humidity and is specifically promoted by contact with an oily or fatty substance or a plasticizer, to an extent such that the faded images cannot be recognized.

Many attempts have been made to retard or inhibit the fading of the colored images formed on a conventional thermosensitive colored image-forming layer containing a substantially colorless dye precursor comprising a lactone ring compound.

For example, Japanese Unexamined Patent Publication Nos. 60-78,782, 59-167,292, 59-114,096 and 59-93,387 disclose a thermosensitive colored image-forming layer containing a phenolic antioxidant.

Japanese Unexamined Patent Publication No. 56-146,794 discloses a protective layer formed from a hydrophobic polymeric compound emulsion on a thermosensitive colored image-forming layer.

Japanese Unexamined Patent Publication No. 58-199,189 discloses formation of both an intermediate layer and a top layer on a thermosensitive colored image-forming layer, and the former being formed from a water-soluble polymeric compound solution or a hydrophobic polymeric compound emulsion and the latter being formed from a solvent-soluble hydrophobic polymer on the intermediate layer.

Japanese Unexamined Patent Publication No. 62-164,579 and No. 60-219,088 disclose a thermosensitive colored image-forming layer containing an additive consisting of an epoxy compound and/or an aziridine compound, which effectively inhibits the fading of the colored images.

In the thermosensitive colored image-forming layer containing the phenolic antioxidant, the resultant colored images exhibit a higher resistance to heat and moisture to a certain extend compared to the colored images formed on a convention colored image-forming layer free from the phenolic antioxidant, but the improvement effect of the phenolic antioxidant is not satisfactorily light. Also, the phenolic antioxidant does not have a capability of enhancing the resistance of the colored images to the oily or fatty substances, for example, salad oil, and plasticizers, for example, dioctyl phthalate. The resistance of the colored images to oily or fatty substance or a plasticizer is determined in such a manner that the colored images are brought into contact with an oily or fatty substance, for example, a salad oil or a plasticizer, and left in contact therewith for a predetermined time, and then a retention of the color density of the tested colored images is measured in comparison with an initial color density thereof.

When the protective layer or the intermediate and surface layers are formed on the thermosensitive colored image-forming layer, the resultant colored images exhibit a significantly enhanced storage persistency when the salad oil or the dioctyl phthalate is brought into contact with the colored image-forming surface of the recording material. Nevertheless, when the salad oil or the dioctyl phthalate is brought into contact with an edge face of the recording material, it penetrates into the inside of the recording material and causes a complete fading of the colored images. Therefore, the provision of the protecting layer or the intermediate and surface layer cannot completely eliminate the undesirable color-fading of the images.

The addition of the epoxy compound and/or aziridine compound to the colored image-forming layer is highly effective to inhibit the fading phenomenon. Nevertheless, this not totally appreciated, because it takes a long time to stabilize the colored images formed on the colored image-forming layer by a heat-recording operation, and therefore, if an oily or fatty substance, for example, salad oil, or a plasticizer, for example, dioctyl phthalate, is brought into contact with the colored image-forming layer immediately after the heat-recording operation, the resultant colored images fade to a great extent.

SUMMARY OF THE INVENTION

An object of the present invention is to provide a thermosensitive recording material capable of forming colored images thereon having an excellent resistance to oily and fatty substances, plasticizers, moisture, and heat, and thus a superior persistency over a long time.

Another object of the present invention is to provide a thermosensitive recording material useful for thermorecording type tickets of automatic ticket machines, for commuter passes, and for coupon tickets, which must have a high persistency of the colored images recorded thereon, and for label sheets to be used in a POS bar code price-indicating system in which the label sheets are attached to a surface of a polyvinyl chloride film containing a plasticizer and wrapping fresh food or meat containing an oily or fatty substance, which label sheets are unavoidably brought into contact with the plasticizer and/or oily or fatty substance.

Further object of the present invention is to provide a thermosensitive recording material useful as facsimile recording sheets, word processor recording sheets, and CRT image printing sheets, which all must have a high persistency of colored images recorded thereon.

The above-mentioned objects can be attained by the thermosensitive recording material of the present invention, which comprises a sheet substrate and a thermosensitive colored image-forming layer formed on a surface of the sheet substrate and comprising a substantially colorless dye precursor, a color developing agent reactive with the dye precursor upon heating to thereby develop a color, and a binder, the color developing agent comprising at least one compound of the formula (I):

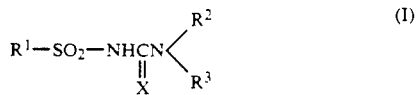

wherein X represents a member selected from the group consisting of oxygen and sulfur atoms, $R^1$ represents a member selected from the group consisting of unsubstituted aromatic cyclic hydrocarbon groups and substituted phenyl groups having at least one substituent selected from the group consisting of lower alkyl groups and halogen atoms, and $R^2$ and $R^3$ respectively and independently from each other represent a hydrogen atom, alkyl groups, aralkyl groups, substituted alkyl groups having an aryloxy group, unsubstituted aromatic cyclic hydrocarbon groups and substituted aromatic cyclic hydrocarbon groups having at least one substituent selected from the group consisting of alkyl groups, aryl groups, aralkyl groups, alkyloxy groups, alkyloxycarbonyl groups, aryloxycarbonyl groups, aralkyloxycarbonyl groups, arylsulfonyl groups and halogen atoms.

In a preferable embodiment of the thermosensitive recording sheet of the present invention, the thermosensitive colored image-forming layer further comprises a colored image-stabilizing agent comprising at least one member selected from the group consisting of organic aziridine compounds having at least one aziridinyl group and aromatic epoxy compounds having at least one epoxy group.

In this specification, the aziridinyl group, i.e., ethyleneimine group, is of the formula:

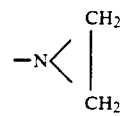

which will be represented hereafter by an abbreviated formula:

Also, the epoxy group is of the formula:

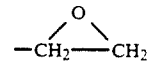

which will be represented hereafter by an abbreviated formula:

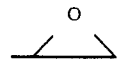

DESCRIPTION OF THE PREFERRED EMBODIMENTS

In the thermosensitive recording material of the present invention, a thermosensitive colored image-forming layer is formed on a surface of a sheet substrate and comprises a substantially colorless dye precursor, a specific color developing agent reactive with the dye precursor upon heating to thereby develop a color, a binder, and, optionally, a specific colored image-stabilizing agent.

The color developing agent comprises at least one N-arylsulfonyl(thio) urea compound of the formula (I).

The compounds of the formula (I) do not have acidic functional groups, for example, a phenolic hydroxyl group or carboxyl group. Nevertheless, the compounds of the formula (I) exhibit a strong color developing ability for the dye precursor consisting of a basic leuco dye. The reasons for the strong color developing ability have not yet been completely made clear, but it is assumed that the (thio) urea group in the compounds of the formula (I) is activated by the sulfonyl group located adjacent to the (thio) urea group.

In the formula (I), the unsubstituted aromatic cyclic hydrocarbon groups standing for $R^1$ include phenyl, naphthyl and anthryl groups.

The lower alkyl groups contained as substituents in the substituted phenyl groups standing for $R^1$ preferably have 1 to 4 carbon atoms and are preferably selected from the group consisting of methyl, ethyl, propyl and butyl groups. The halogen atoms in the substituted phenyl groups are selected from F, Cl, Br and I. With respect to $R^2$ and $R^3$ in the formula (I), preferably, the alkyl groups have 1 to 8 carbon atoms and are selected from methyl, ethyl, propyl, butyl, pentyl, hexyl, and octyl; the aralkyl groups are preferably selected from benzyl phenetyl and methyl benzyl groups; the aryloxy group-substituted alkyl groups are selected from phenoxy methyl, phenoxy ethyl and nathoxy ethyl groups; the unsubstituted aromatic cyclic hydrocarbon groups are selected from phenyl, naphthyl, and anthryl groups; and the substituted aromatic cyclic hydrocarbon groups are selected from substituted phenyl, naphthyl, and anthryl groups having at least one substituent as defined above.

With respect to the substituent of the substituted aromatic cyclic hydrocarbon groups standing for $R^2$ and $R^3$, preferably, the alkyl groups have 1 to 4 carbon atoms are selected from methyl, ethyl, propyl, and butyl groups; the aryl groups are selected from phenyl and naphthyl groups; the aralkyl groups are selected from benzyl, phenetyl, and methyl benzyl; the alkyloxy groups are selected from methoxy, ethoxy, propoxy, and butoxy groups; the alkyloxycarbonyl groups are selected from $CH_3OCO-$, $C_2H_5OCO-$, $C_3H_7OCO-$, and $C_4H_9OCO-$ groups; the aryloxycarbonyl groups are selected from $C_6H_5OCO-$, $CH_3C_6H_5OCO-$, $CH_3O-C_6H_5OCO-$, and naphthyloxycarbonyl groups; the aralkyloxycarbonyl groups are selected from $C_6H_5CH_2OCO-$, $CH_3-C_6H_5CH_2OCO-$, and naphthylmethyloxycarbonyl groups; the arylsulfonyl groups are selected from $C_6H_5SO_2-$, $CH_3C_6H_5SO_2-$, and naphthylsulfonyl groups; and the halogen atoms are selected from F, Cl, Br, and I.

The color developing N-arylsulfonyl(thio)urea compound of the formula (I) is preferably selected from the group consisting of:

N-(p-toluenesulfonyl)-N'-phenylurea (m.p.: 165° C.), N-(p-toluenesulfonyl)-N'-(p-methoxyphenyl)urea (m.p.: 155° C.), N-(p-toluenesulfonyl)-N'-(o-tolyl)urea (m.p.: 148° C.), N-(p-toluenesulfonyl)-N'-(m-tolyl)urea (m.p.: 184° C.), N-(p-toluenesulfonyl)-N'-(p-tolyl)urea (m.p.: 149° C.), N-(p-toluenesulfonyl)-N'-(p-n-butylphenyl-)urea (m.p.: 177° C.), N-(p-toluenesulfonyl)N-(p-toluenesulfonyl)N',N'-diphenylurea (m.p.: 159° C.), N-(p-toluenesulfonyl)-N'-(o-chlorophenyl)urea (m.p.: 180° C.), N-(p-toluenesulfonyl)-N'-(m-chlorophenyl-)urea (m.p.:193° C.), N-(p-toluenesulfonyl)-N'-(2,4-dichlorophenyl)urea, N-(p-toluenesulfonyl)-N'-methyl-N'-phenylurea (m.p.: 155° C.), N-(p-toluenesulfonyl)-N'-benzylurea (m.p.: 177° C.), N-(p-toluenesulfonyl)-N'-(1-naphthyl)urea (m.p.: 124° C.), N-(p-toluenesulfonyl)-N'-(1-(2-methylnaphthyl))urea, N-(benzenesulfonyl)-N'-phenylurea (m.p.: 153° C.), N-(p-chlorobenzenesulfonyl)N'-phenylurea, N-(o-toluenesulfonyl)-N'-phenylurea, N-(p-toluenesulfonyl)-N'- methylurea (m.p.: 172° C.), N-(p-toluenesulfonyl)-N'- ethylurea (m.p.: 141° C.), N-(p-toluenesulfonyl)-N'-(2-phenoxyethyl)urea (m.p.: 191° C.), N,N'-bis(p-toluenesulfonyl-)urea (m.p.: 155° C.), N-(p-toluenesulfonyl)-N'-phenylthiourea, N-(p-toluenesulfonyl)-N'-(o-diphenyl)urea (m.p.: 148° C.), and N-(p-toluenesulfonyl)-N'-(p-ethoxycarbonylphenyl)urea.

The above-mentioned compounds of the formula (I) can be employed alone or as a mixture of two or more of those compounds.

Some of the N-arylsulfonyl(thio)urea compounds of the formula (I) are novel compounds. The compounds of the formula (I) can be prepared in accordance with the following reactions (1) to (4):

Reaction (1):

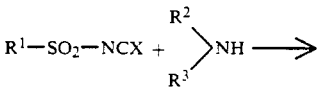

Reaction (2):

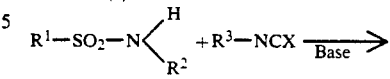

Compound of the formula (I)

Reaction (3):

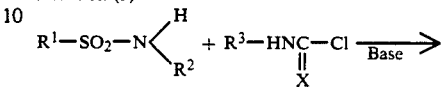

Compound of the formula (I)

Reaction (4):

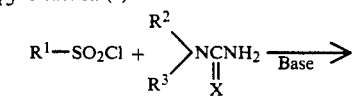

Compound of the formula (I)

In the above-mentioned formulae, $R^1$, $R^2$, $R^3$, and X are as defined for the formula (I).

In a preferable embodiment of the present invention, the thermosensitive colored image-forming layer comprises a colored image-stabilizing agent in addition to the dye precursor, the color-developing agent, and the binder.

The colored image-stabilizing agent comprises at least one member selected from the organic aziridinyl compound and the aromatic epoxy compounds.

The aziridine compounds usable for the present invention are preferably selected from the group consisting of 2,4-bis(1-aziridinylcarbonylamino)toluene, bis(4-(1-aziridinylcarbonylamino phenyl)methane, bis(3-chloro-4-(1-aziridinylcarbonylamino)phenyl), methane, 2,2-bis(4-(1-aziridinylcarbonyloxy)phenyl)propane, 1,4-bis(1-aziridinylcarbonyloxy)benzene, and 1,4-bis(1-aziridinyl-carbonyl)benzene.

Also, the aromatic epoxy compounds usable for the present invention are preferably selected from the group consisting of 4,4'-bis(2",3"-epoxypropyloxy) diphenylsulfone, 2,2-bis(4'-(2",3"-epoxypropyloxy)phenyl) propane, 1,4-bis(2'3"-epoxypropoloxy)benzene, 4-(2'-methyl-2'3"-epoxypropyloxy)-4,-benzyloxy-diphenylsulfone, 4-(2",3"-epoxypropyloxy)-4'-(p-methyl-benzyloxy)diphenylsulfone, epoxidized o-novolak cresol resins, 4,4'-bis(2",3"-epoxypropyloxy)diphenylmethane, 4,4'-bis (2",3"-epoxypropylamino)diphenylmethane, bis(2",3"-epoxypropyl) 4,4'-methylene-dibenzoate, 4,4'-bis(2",3"-epoxypropyloxy)biphenyl, 4,4'-bis(-2",3"-epoxypropyloxy) 3,3'5,5'-tetramethylbiphenyl, 2,6-bis(2,'3'-epoxypropyloxy)naphthalene, and bis(2,3-epoxypropyl) terephthalate.

The dye precursor usable for the present invention comprises at least one member selected from conventional triphenylmethane, fluoran, and diphenylmethane leuco dyes, for example, 3-(4-diethylamino-2-ethoxyphenyl)-3-(1-ethyl-2-methylindole-3-Y1)-4-azaphthalide, crystal violet lactone, 3-(N-ethyl-N-isopentylamino)-6-methyl-7-anilinofluoran, 3-diethylamino-6-methyl-7-anilinofluoran, 3-diethylamino-6-methyl-7-(2',4'-dimenthyl-anilino) fluoran, 3-(N-ethyl-N-p-toluidino)-6-methyl-7-anilinofluoran, 3-pyrrolidino-6-methyl-7-anilinofluoran, 3-dibutylamino-6-methyl-7-anilinofluoran, 3-(N-cyclohexyl-N-methylamino)-6-methyl-7-anilinofluoran, 3-diethylamino-7-(o-chloroanilino)fluoran, 3-diethylamino-7-(m-trifluoromethylanilino)fluoran, 3-diethylamino-6-methyl-7-chlorofluoran, 3-diethylamino-6-methylfluoran, 3-cyclohexylamino-6-clorofluoran and 3-(N-ethyl-N-hexylamino)-6-methyl-7-(p-chloroanilino) fluoran.

In the thermosensitive colored image-forming layer of the present invention, the color developing agent optionally contains at least one conventional color-developing compound in addition to the N-arylsufonyl(thio) urea compound of the formula (I), unless the color-forming performance of the colored image-forming layer is disturbed thereby.

The conventional color developing compound is preferably selected from the group consisting of 2,2-bis(4-hydroxyphenyl)propane (namely bisphenol A), 1,1-bis(4-hydroxyphenyl)-1-phenylethane, 1,4-bis(1-methyl-1-(4'-hydroxyphenyl)ethyl)benzene, 1,3-bis(1-methyl-1-(4,hydroxyphenyl)ethyl)benzene, dihydroxydiphenylether (disclosed in JP-A-1-180,382), benzyl p-hydroxy-benzoate (disclosed in JP-A-52-140,483), bisphenol S, 4-hydroxy-4'-isopropyl-oxydiphenylsulfone (disclosed in JP-A-60-13,852), 1,1-di-(4-hydroxyphenyl)-cyclohexane, 1,7-di(4-hydroxyphenylthio)-3,5-dioxaheptane (disclosed in JP-A-59-52,694), and 3,3,-diallyl-4,4'-dihydroxydiphenylsulfone (disclosed in JP-A-60-208,286).

The above-mentioned conventional color developing compounds can be employed alone or as a mixture of two or more thereof.

The binder usable for the present invention preferably comprises at least one member selected from water-soluble polymeric materials, for example, various types of polyvinyl alcohols which have a different molecular weight from each other, starch and starch derivatives, cellulose derivatives, for example, methoxy cellulose, carboxymethyl cellulose, methyl cellulose and ethyl cellulose, sodium polyarcylate, polyvinyl pyrrolidine, acrylic acid amide-acrylic acid ester copolymers, acrylic acid amide-acrylic acid ester-methacrylic acid terpolymers, alkali salts of styrene-maleic anhydride copolymers, polyacrylic acid amide, sodium alginate, gelatine and casein, and water-insoluble polymeric materials, for example, polyvinyl acetate resins, polyurethane resins, styrene-butadiene copolymer resins, polyacrylic acid resins, polyacrylic acid ester resins, vinyl chloride-vinyl acetate copolymer resins, polybutyl acrylate, ethylene-vinyl acetate copolymer resins and styrene-butadiene-acrylic compound-terpolymer resins, used in the form of a latex.

In the thermosensitive colored image-forming layer of the present invention, the dye precursor is present in an amount of 5 to 20% of weight, the color developing compound of the formula (I) is present in an amount of 10 to 50% by weight, and the binder is present in an amount of 5 to 20% by weight, based on the total dry weight of the colored image-forming layer.

When the content of the color developing compound of the formula (I) is less than 10% by weight, the resultant thermosensitive colored image-forming layer exhibits an unsatisfactory color-forming performance, and when the content of the color developing compound of the formula (I) is more than 50% by weight, the resultant color-developing performance is saturated, and thus the resultant recording material is sometimes economically disadvantageous.

The color developing agent contains the N-arylsulfonyl(thio)urea compound of the formula (I) in an amount of 30% to 100% by weight and the conventional color developing compound in an amount of 0 to 70% by weight.

Also, in the thermosensitive colored image-forming layer, the colored image-stabilizing agent is preferably present in an amount of 1 to 30% based on the total dry weight of the colored image-forming layer.

A content of less than 1% by weight of the color image stabilizing agent causes an unsatisfactory colored image-stabilizing effect, and a content of more than 50% by weight results in a saturated colored image-stabilizing effect, and thus in an economical disadvantage.

The thermosensitive colored image-forming layer of the present invention optionally further comprises a heat-fusible organic substance, usually referred to as a sensitizer, inorganic and organic pigments, antioxidants, for example, hindered phenol compounds, ultraviolet ray-absorbers, and waxes.

The sensitizing agent comprises at least one organic compound having a melting point of from 50° C. to 150° C., for example, phenyl 1-hydroxy-2-naphthoate (JP-A-57-191,089), p-benzyl-biphenyl (JP-A-60-82,382), benzyl naphthyl ether (JP-A-58-87,094), dibenzyl terephthalete (JP-A-58-98,285), benzyl p-benzyloxybenxoate (JP-A-57-201,691), diphenyl carbonate, ditolyl carbonate (JP-A-58-136,489), m-terphenyl (JP-A-57-89,994), 1,2-bis(m-tolyloxy)ethane (JP-A-60-56,588), 1,5-bis(p-methoxyphenoxy)-3-oxapentane (JP-A-62-181,183), oxalic acid diesters (JP-A-64-1,583) and 1,4-bis(p-tolyloxy) benzene (JP-A-2-153,783).

The antioxidant and ultraviolet ray-absorbers are preferably selected from those disclosed in JP-A-57-151,394, JP-A-58-160,191, JP-A-58-69,096, JP-A-59-2,884, JP-A-59-95,190, JP-A-60-22,288, JP-A-60-255,485, JP-A-61-44,686, JP-A-62-169,683, JP-A-63-17,081 and JP-A-1-249,385, for example, 1,1,3-tris(3'-cyclohexyl-4'-hydroxyphenyl)butane; 1,1,3-tris(2-methyl-4-hydroxy-5-tert-butylphenyl)butane, 4,4-thio-bis(3-methyl-6-tertbutylphenol), 1,3,5-trimethyl-2,4,6-tris(3,5-di-tertbutyl-4-hydroxybenzyl)benzene, 2,2'-dihydroxy-4, 4'-dimethoxybenzophenone, p-octylphenyl salycilate, 2-(2'-hydroxy-5'-methylphenyl)benzotriazole, ethyl-2-cyano-3,3'-diphenyl acrylate, and tetra(2,2,6,6-tetramethyl-4-piperidyl)-1,2,3,4-butane-tetra-carbonate.

The waxes usable for the present invention preferably comprises at least one member selected from, for example, paraffin waxes, carnauba wax, microcrystalline waxes, polyethylene waxes, amide type waxes, bisimide type waxes, higher fatty acid amide waxes, for example, stearic acid amide, ethylene-bis-stearoamide wax, higher fatty acid esters and metal salts, for example, zinc stearate, aluminum stearate, calcium stearate, and zinc oleate.

The inorganic and organic pigments usable for the present invention are preferably selected from inorganic fine particles of, for example, calcium carbonate, silica, zinc oxide, titanium dioxide, aluminum hydroxide, zinc hydroxide, barium sulfate, clay, anhydrous clay, talc, and surface-treated calcium carbonate and silica and organic fine particles of, for example, urea-formaldehyde resins, styrene-methacrylate copolymer resins and polystyrene resins.

In the colored image forming layer of the present invention, the sensitizing agent is preferably contained in an amount of 5 to 40% by weight, the wax and organic or inorganic pigment are optionally contained in amounts of 2 to 20% by weight and 5 to 50% by weight, respectively, and the antioxidant and ultraviolet ray-absorber are contained preferably in an amount of 1 to 10%, based on the total dry weight of the colored image-forming layer.

The sheet substrate usable for the present invention is not limited to a specific group of materials, and usually the sheet substrate comprises a member selected from fine paper sheets, coated paper sheets having a clay or latex-coated layer, cast-coated paper sheets, paper boards, plastic resin films, synthetic paper sheets comprising a plastic resin such as a polyolefin resin and a multi-layer structure, and laminated composite sheets. Preferably, the sheet substrate has a basis weight of 40 to 170 g/m².

The colored image-forming layer can be formed on a surface of sheet substrate, by applying a coating liquid containing the above-mentioned components, and by drying and solidifying the coating liquid layer on the sheet substrate.

The colored image-forming layer is preferably present in a dry weight of from 1 to 15 g/m², more preferably 2 to 10 g/m².

In the present thermosensitive recording material, a protective layer and/or a layer for printing may be formed on the colored image-forming layer.

In the thermosensitive recording material of the present invention, the novel color developing compounds of the formula (I) exhibit a color-developing activity comparative to or higher than that of bisphenol A which is a typical conventional color developing compound.

Also, when the color developing compound of the formula (I) is present together with the colored image-stabilizing agent consisting of the aziridinyl compound and/or the epoxy compound, the resultant colored images exhibit an excellent resistance to oily and fatty substances and a plasticizer even immediately after the color development, and thus have a superior storage persistency.

EXAMPLES

The present invention will be further explained by the following specific examples, which are merely representative and do not in any way restrict the scope of the present invention.

Synthesis Example 1 (Preparation of
N-(p-toluenesulfonyl)-N'-phenylurea)

A three-necked flask equipped with a dropping funnel, a thermometer, and a reflux condenser was charged with 18.6 g of aniline and the aniline was dissolved in 200 ml of toluene. While the resultant reaction solution was stirred with a magnetic stirrer, 42.0 g of toluenesulfonylisocyanate were added dropwise from the dropping funnel to the reaction solution. During the stirring, an exothermic reaction occurred and a large amount of white solid was precipitated. The resultant reaction mixture was heated at a temperature of 90° C. for one hour, cooled, and then filtered. White crystals were obtained in an amount of 58.0 g. The crystals had a melting point of 166° C.

NMR measurement, mass spectrometric analysis, and IR measurement identified the resultant crystals as the aimed compound.

Synthesis Example 2 (Preparation of N-(p-toluenesulfonyl)-N'-(o-tolyl)urea)

The same synthesis procedures were carried out, with the following exceptions.

The aniline in the amount of 18.6 g was replaced by 10.7 g of o-toluidine, and the toluenesulfonylisocyanate was employed in an amount of 20.7 g. The resultant white crystals were in an amount of 30.0 g and had a melting point of 148° C.

NMR measurement, mass spectrometric analysis, and IR measurement confirmed that the resultant product was the aimed compound.

Synthesis Example 3 (Preparation of N-(p-toluenesulfonyl)-N'-(p-tolyl)urea)

The same synthesis procedures as in Synthesis Examples 12 were carried out, with the following exceptions.

The aniline in the amount of 18.6 g was replaced by 10.7 g of p-toluidine.

The resultant white crystals were in an amount of 29.6 g and exhibited a melting point of 149° C.

NMR measurement, mass spectrometric analysis, and IR measurement confirmed that the resultant product was the aimed compound.

Synthesis Example 4 (Preparation of N-(benzenesulfonyl)-N'-phenylurea)

A three-necked flask equipped with a dropping funnel, a thermometer, and a reflux condenser was charged with 6.3 g of benzenesulfonamide. The benzenesulfonamide was dissolved in a mixed solvent consisting of 10 ml of pyridine and 10 ml of tetrahydrofuran. To the resultant reaction solution was added dropwise 5.0 g of phenylisocyanate from the dropping funnel, while stirring the solution by using a magnetic stirrer. The reaction solution was heat-stirred at the reflux temperature for 3 hours. After the completion of the reaction procedures, the resultant reaction mixture was poured into water and the pH of the resultant aqueous mixture was adjusted to a slightly acidic side by adding a diluted hydrochloric acid aqueous solution, to allow white crystals to be precipitated. The white crystals were collected by filtration, and then dried. The dried white crystals were in an amount of 10.6 g and exhibited a melting point of 153° C.

NMR measurement, mass spectrometric analysis, and IR measurement confirmed that the resultant product was the aimed compound.

EXAMPLE 1

A thermosensitive recording paper sheet was prepared by the following procedures.

(1) Preparation of an aqueous dye precursor dispersion A in the following composition

| Component | Part by weight |
| --- | --- |
| 3-(N-isopentyl-N-ethylamino)-6-methyl-7-anilinofluoran | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(2) Preparation of an aqueous color-developing agent discersion B in the following composition

| Component | Part by weight |
| --- | --- |
| N-(p-toluenesulfonyl)-N'-(p-tolyl)urea | 10 |
| | 10 |

-continued

| Component | Part by weight |
| --- | --- |
| 10% aqueous solution of polyvinyl alcohol | 10 |
| Water | 70 |

The composition was dispersed in a sand grinder to an extent such that the resultant dispersed solid particles had an average size of 1 μm or less.

(3) Preparation of a pigment-coated paper sheet

A coating liquid was prepared by mixing an aqueous dispersion, prepared by dispersing 85 parts by weight of anhydrous clay available under the trademark of Ansilex, from Engelhard Corporation, in 320 parts by weight of water, with 40 parts by weight of an aqueous emulsion of a styrene-butadiene copolymer in a solid concentration of 50% by weight and 50 parts by weight of a 10% aqueous oxidized starch solution.

The coating liquid was coated on a surface of a fine paper sheet having a basis weight of 48 g/m², to form a coating layer having a dry weight of 7.0 g/m², whereby a coated paper sheet was obtained.

(4) Formation of thermosensitive colored image-forming layer

A coating liquid was prepared by evenly mixing 50 parts by weight of the aqueous dye precursor dispersion A and 200 parts by weight of the aqueous color-developing agent dispersion B with 33 parts by weight of a calcium carbonate pigment, 20 parts by weight of a 25% aqueous zinc stearate dispersion, 15 parts by weight of 30% aqueous paraffin dispersion, and 120 parts by weight of a 10% aqueous polyvinyl alcohol solution, by agitating the mixture.

A surface of the pigment coated paper sheet was coated with the resultant coating liquid and dried. A thermosensitive colored image-forming layer was formed in a weight of 5.0 g/m², to provide a thermosensitive recording paper sheet.

The recording sheet was treated by a super calender, and the calendered surface of the recording sheet had a Bekk smoothness of 600 to 1000 seconds.

A specimen of the resultant thermosensitive recording sheet was subjected to a colored image-developing test by using a dynamic color-developing tester provided by modifying a thermosensitive facsimile printer with an applied energy of 0.39 mj/dot. The resultant black colored images were subjected to a measurement of a color density by a Macbeth Reflection Color Density Tester RD-914 (trademarks).

Also, the whiteness of the non-image-formed white portions of the recording sheet was measured by using a Hunter whiteness tester with a blue filter.

The test results are shown in Table 1.

EXAMPLE 2

A thermosensitive recording sheet was produced and tested by the same procedures as in Example 1 except that, in the preparation of the dispersion B, the N-(p-toluenesulfonyl)-N'-(p-tolyl)urea was replaced by N-(p-toluenesulfonyl)-N'-phenylurea, and di-p-methylbenzyl oxalate was replaced by dibenzyl oxalate.

The test results are shown in Table 1.

COMPARATIVE EXAMPLE 1

A thermosensitive recording sheet was produced and tested by the same procedures as in Example 1 except that, in the preparation of the dispersion B, the N-(p-toluenesulfonyl)-N'-(p-tolyl)urea was replaced by 2,2-bis(4-hydroxyphenyl)propane (namely bisphenol A).

The test results are shown in Table 1.

COMPARATIVE EXAMPLE 2

A thermosensitive recording sheet was produced by the same procedures as in Example 1 except that, in the preparation of the dispersion B, the N-(p-toluenesulfonyl)-N'-(p-tolyl)urea was replaced by N,N'-diphenyl urea.

The test results are shown in Table 1.

TABLE 1

| Example No. | Item Color density (D) of colored images |
| --- | --- |
| Example | |
| 1 | 1.41 |
| 2 | 1.45 |
| Comparative Example | |
| 1 | 1.35 |
| 2 | 0.83 |

EXAMPLE 3

A thermosensitive recording sheet was produced by the same procedures as in Example 1, with the following exceptions.

(1) Preparation of an aqueous dispersion C of a colored image-stabilizing agent in the following composition

| Component | Part by weight |
| --- | --- |
| bis(4-(1-aziridinylcarbonyl amino)phenyl)methane | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(2) Formation of thermosensitive colored image-forming layer

A coating liquid was prepared by evenly mixing 50 parts by weight of the aqueous dye precursor dispersion A and 200 parts by weight of the aqueous color developing agent dispersion B mentioned in Example 1 and parts by weight of the above-mentioned aqueous colored image-stabilizing agent dispersion C with 23 parts by weight of a calcium carbonate pigment, 20 parts by weight of a 25% aqueous zinc stearate dispersion, 15 parts by weight of a 30% aqueous paraffin dispersion, and parts by weight of a 10% aqueous polyvinyl alcohol solution, by agitating the mixture.

A surface of the pigment-coated paper sheet as mentioned in Example 1 was coated with the resultant coating liquid and dried to form a thermosensitive colored image-forming layer having a dry weight of 5.0 g/m², thereby to provide a thermosensitive recording sheet.

The recording sheet was treated by a super calender to provide a calendered surface thereof having a Bekk smoothness of 600 to 1,000 seconds.

A specimen of the resultant calendered recording sheet was subjected to the same colored image-developing test and color density measurement test as in Example 1.

Specimens of the color image-formed recording sheet were subjected to an oily substance or plasticizer resistance test in the following manner.

Within 30 minutes from the completion of the color developing operation or 5 hours after the completion of the color developing operation, a colored image-formed surface of a specimen was coated with a salad oil or dioctyl terephthalate, which is a typical plasticizer, and left to stand at room temperature for 3 hours. Then, the salad oil or plasticizer was wiped away from the specimen and the color density of the colored images retained on the specimen was measured by a Macbeth Reflection Color Density Tester. The measured color density represents a resistance of the colored images to the salad oil or plasticizer.

The test results are shown in Tables 2 and 3.

EXAMPLE 4

A thermosensitive recording sheet was produced by the same procedures as in Example 3 except that, in the preparation of the dispersion B, the N-(p-toluenesulfonyl)-N'-(p-tolyl)urea was replaced by N-(p-toluenesulfonyl)-N'-(o-tolyl) urea.

The test results are shown in Tables 2 and 3.

EXAMPLE 5

A thermosensitive recording sheet was produced by the same procedures as in Example 3 except that, in the preparation of the dispersion C, the bis(4-(1-aziridinylcarbonylamino)phenyl)methane was replaced by 2,4-bis(1-aziridinylcarbonylamino)toluene.

The test results are shown in Tables 2 and 3.

EXAMPLE 6

A thermosensitive recording sheet was produced by the same procedures as in Example 3 except that, in the formation of the thermosensitive colored image-forming layer, a coating liquid prepared by stir-mixing 40 parts by weight of the dispersion A, 120 parts by weight of the dispersion B, and 40 parts by weight of the dispersion C with 43 parts by weight of a calcium carbonate pigment, 20 parts by weight of a 25% aqueous zinc stearate dispersion, 15 parts by weight of a 30% aqueous paraffin dispersion, and 120 parts by weight of a 10% aqueous polyvinyl alcohol solution was applied to a surface of a paper sheet having a basis weight of 48 g/m², and dried to form a thermosensitive colored image-forming layer having a dry weight of 7.0 g/m². A thermosensitive recording sheet was obtained.

The test results are shown in Tables 2 and 3.

EXAMPLE 7

A thermosensitive recording sheet was produced by the same procedures as in Example 3, with the following exceptions.

In the preparation of the dispersion A, the 3-(N-isopentyl-N-ehtylamino)-6-methyl-7-anilinofluoran was replaced by 3-dibutyl-amino-6-methyl-7-anilinofluoran.

Also, in the preparation of the dispersion B, the N-(p-toluenesulfonyl)-N'-(p-tolyl)urea was replaced by N-(p-toluenesulfonyl)-N'-phenylsaulfonylurea.

The test results are shown in Tables 2 and 3.

COMPARATIVE EXAMPLE 3

A thermosensitive recording sheet was produced by the same procedures as in Example 3 except that, in the preparation of the dispersion B, the N-(p-toluenesulfonyl)-N'-(p-tolyl)urea was replaced by 2,2-bis(4-hydroxyphenyl)propane (namely bisphenol A).

The test results are shown in Tables 2 and 3.

TABLE 2

| | Item | | |
|---|---|---|---|
| | | Colored density (D') of remaining colored image after salad oil application test | |
| Example No. | Color density (D) of original colored image | Applied within 30 minutes from color development | Applied 5 hours after color development |
| Example | | | |
| 3 | 1.39 | 1.17 | 1.34 |
| 4 | 1.31 | 1.09 | 1.26 |
| 5 | 1.36 | 1.16 | 1.31 |
| 6 | 1.29 | 1.10 | 1.24 |
| 7 | 1.34 | 1.13 | 1.29 |
| Comparative Example 3 | 1.31 | 0.39 | 0.89 |

TABLE 3

| | Item | | |
|---|---|---|---|
| | | Colored density (D') of remaining colored image after plasticizer application test | |
| Example No. | Color density (D) of original colored image | Applied within 30 minutes from color development | Applied 5 hours after color development |
| Example | | | |
| 3 | 1.39 | 0.82 | 1.03 |
| 4 | 1.31 | 0.79 | 0.97 |
| 5 | 1.34 | 0.91 | 1.00 |
| 6 | 1.29 | 0.77 | 0.99 |
| 7 | 1.33 | 0.75 | 0.94 |
| Comparative Example 3 | 1.31 | 0.30 | 0.66 |

Tables 1, 2, and 3 clearly show that in the thermosensitive colored image-forming layer of the present invention, the N-arylsulfonyl(thio)urea compound of the formula (I) exhibits a satisfactory color developing ability comparative to or higher than that of bisphenol A which is a typical conventional color developing agent, and the combination of the specific color developing compound of the formula (I) with the aromatic aziridine compound highly effectively causes the resultant colored images to exhibit an excellent resistance to oily and fatty substances and plasticizers, even immediately after the color development.

EXAMPLE 8

A thermosensitive recording paper sheet was prepared by the following procedures.

(1) Preparation of an aqueous dye precursor dispersion A in the following composition

| Component | Part by weight |
|---|---|
| 3-(N-isopentyl-N-ethylamino)-6-methyl-7-anilinofluoran | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(2) Preparation of an aqueous color-developing agent dispersion B in the following composition

| Component | Part by weight |
| --- | --- |
| N-(p-toluenesulfonyl)-N'-phenylurea | 10 |
| Di-p-methylbenzyl oxalate | 10 |
| 10% aqueous solution of polyvinyl alcohol | 10 |
| Water | 70 |

The composition was dispersed in a sand grinder to an extent such that the resultant dispersed solid particles had an average size of 1 μm or less.

(3) Preparation of an aqueous dispersion C of a colored image-stabilizing agent in the following composition

| Component | Part by weight |
| --- | --- |
| 4,4'-bis(2'',3''-epoxypropyloxy)diphenylsulfone | 20 |
| 10% aqueous polyvinyl alcohol solution | 10 |
| Water | 70 |

The composition was dispersed in a sand grinder to an extent such that the resultant dispersed solid particles had an average size of 1 μm or less.

(4) Preparation of a pigment-coated paper sheet

A coating liquid was prepared by mixing an aqueous dispersion, prepared by dispersing 85 parts by weight of anhydrous clay available under the trademark of Ansilex, from Engelhard Corporation, in 320 parts by weight of water, with 40 parts by weight of an aqueous emulsion of a styrene-butadiene copolymer in a solid concentration of 50% by weight and 50 parts by weight of a 10% aqueous oxidized starch solution.

The coating liquid was coated on a surface of a fine paper sheet having a basis weight of 48 g/m$^2$, to form a coating layer having a dry weight of 7.0 g/m$^2$, whereby a coated paper sheet was obtained.

(5) Formation of thermosensitive colored image-forming layer

A coating liquid was prepared by evenly mixing 50 parts by weight of the aqueous dye precursor dispersion A, 200 parts by weight of the aqueous color-developing agent dispersion B, and 50 parts by weight of the aqueous colored image-stabilizing agent dispersion C with 23 parts by weight of a calcium carbonate pigment, 20 parts by weight of a 25% aqueous zinc stearate dispersion, 15 parts by weight of 30% aqueous paraffin dispersion, and 120 parts by weight of a 10% aqueous polyvinyl alcohol solution, by agitating the mixture.

A surface of the pigment coated paper sheet was coated with the resultant coating liquid and dried. A thermosensitive colored image-forming layer was formed in a weight of 5.0 g/m$^2$, to provide a thermosensitive recording paper sheet.

The recording sheet was treated by a super calender, and the calendered surface of the recording sheet had a Bekk smoothness of 600 to 1000 seconds.

A specimen of the resultant thermosensitive recording sheet was subjected to a whiteness measurement by a Hunter Whiteness Tester with a blue filter, and to a colored image-developing test by using a dynamic color-developing tester provided by modifying a thermosensitive facsimile printer with an applied energy of 0.39 mj/dot. The resultant black colored images were subjected to a measurement of a color density thereof by the Macbeth Reflection Color Density Tester RD-914.

A specimen of the colored image-formed sheet was coated with salad oil and left to stand for 3 hours. Then, the salad oil was wiped away from the specimen and the color density D' of the remaining colored image was determined by using a Macbeth Reflection Color Density Tester. The storage persistency of the colored image was represented by the measured color density D'.

The test results are shown in Table 4.

EXAMPLE 9

A thermosensitive recording sheet was prepared and tested by the same procedures as in Example 8 except that, in the preparation of the dispersion B, the N-(p-toluenesulfonyl)-N'-phenylurea was replaced by N-(p-toluenesulfonyl)-N'-(p-tolyl)urea.

The test results are shown in Table 4.

EXAMPLE 10

A thermosensitive recording sheet was produced and tested by the same procedures as in Example 8 except that, in the preparation of the dispersion C, the 4,4'-bis(2'',3''-epoxypropyloxy)diphenylsulfone was replaced by bis(2,3-epoxypropyl)terephthalate.

The test results are shown in Table 4.

EXAMPLE 11

A thermosensitive recording sheet was produced and tested by the same procedures as in Example 8 except that, in the preparation of the dispersion C, the 4,4'-bis(2'',3''-epoxypropyloxy)diphenylsulfone was replaced by 4-(2'-methyl-2',3'-epoxypropyloxy)-4'-benzyloxydiphenylsulfone.

The test results are shown in Table 4.

EXAMPLE 12

A thermosensitive recording sheet was produced and tested by the same procedures as in Example 8 except that, the 4,4'-bis(2'',3''-epoxypropyloxy)diphenylsulfone was replaced by an epoxidized o-novolak cresol resin dispersion (available under the trademark of Denacol EM-125, from Nagase Kasei K.K.)

The test results are shown in Table 4.

EXAMPLE 13

A thermosensitive recording sheet was produced by the same procedures as in Example 8 except that, in the formation of the thermosensitive colored image-forming layer, a coating liquid prepared by stir-mixing 40 parts by weight of the dispersion A, 120 parts by weight of the dispersion B, and 40 parts by weight of the dispersion C with 43 parts by weight of a calcium carbonate pigment, 20 parts by weight of a 25% aqueous zinc stearate dispersion, 15 parts by weight of a 30% aqueous paraffin dispersion, and 120 parts by weight of a 10% aqueous polyvinyl alcohol solution was applied to a surface of a paper sheet having a basis weight of 48 g/m$^2$, and dried to form a thermosensitive colored image-forming layer having a dry weight of 7.0 g/m$^2$. A thermosensitive recording sheet was obtained.

The test results are shown in Table 4.

EXAMPLE 14

A thermosensitive recording sheet was produced by the same procedures as in Example 8 except that, in the preparation of the dispersion A, the 3-(N-isopentyl-N-ethylamino)-6-methyl-7-anilinofluoran was replaced by 3-dibutyl-amine-6-methyl-7-anilinofluoran.

The test results are shown in Table 4.

COMPARATIVE EXAMPLE 4

A thermosensitive recording sheet was produced and tested by the same procedures as in Example 8 except that, in the preparation of the dispersion B, the N-(p-toluenesulfonyl)-N'-phenylurea was replaced by 2,2-bis(4-hydroxyphenyl)propane (namely bisphenol A).

The test results are shown in Table 4.

TABLE 4

| | Item | | |
|---|---|---|---|
| Example No. | Whiteness of recording sheet (%) | Color density (D) of original colored image | Color density (D') of remaining colored image after salad oil application test |
| Example | | | |
| 8 | 79.2 | 1.32 | 0.94 |
| 9 | 77.8 | 1.34 | 0.91 |
| 10 | 78.1 | 1.32 | 0.86 |
| 11 | 80.0 | 1.31 | 0.85 |
| 12 | 80.4 | 1.33 | 0.89 |
| 13 | 77.1 | 1.25 | 0.92 |
| 14 | 84.0 | 1.26 | 0.81 |
| Comparative Example 4 | 69.3 | 1.31 | 0.77 |

Table 4 clearly indicates that the colored image-forming layer of the present invention containing the color developing N-arylsulfonyl(thio)urea compound of the formula (I) and the aromatic epoxy compound exhibits a satisfactory whiteness and causes the resultant colored images formed thereon to exhibit an enhanced oil resistance and storage persistency.

We claim:

1. A thermosensitive recording material comprising: a sheet substrate and a thermosensitive colored image-forming layer formed on a surface of the sheet substrate and comprising a substantially colorless dye precursor, a color developing agent reactive with the dye precursor upon heating to thereby develop a color, and a binder, said color developing agent comprising at least one compound of the formula (I):

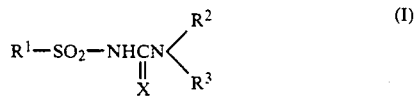

wherein X represents a member selected from the group consisting of oxygen and sulfur atoms, $R^1$ represents a member selected from the group consisting of unsubstituted aromatic hydrocarbon groups and substituted phenyl groups having at least one substituent selected from the group consisting of lower alkyl groups and halogen atoms, and $R^2$ and $R^3$ respectively and independently from each other represent a hydrogen atom, alkyl groups, aralkyl groups, substituted alkyl groups having an aryloxy group, unsubstituted aromatic cyclic hydrocarbon groups and substituted aromatic hydrocarbon groups having at least one substituent selected from the group consisting of alkyl groups, aryl groups, aralkyl groups, alkyloxy groups, alkyloxycarbonyl groups, aryloxycarbonyl groups, aralkyloxycarbonyl groups, arylsulfonyl groups, and halogen atoms.

2. The thermosensitive recording materials as claimed in claim 1, wherein the thermosensitive colored image-forming layer further comprises a colored image-stabilizing agent comprising at least one member selected from the group consisting of organic aziridine compounds having at least one aziridinyl group and aromatic epoxy compounds having at least one epoxy group.

3. The thermosensitive recording material as claimed in claim 2, wherein the colored image-stabilizing agent is present in an amount of 1 to 30% based on the total dry weight of the thermosensitive colored image-forming layer.

4. The thermosensitive recording material as claimed in claim 2, wherein the aziridine compounds for the colored image-stabilizing agent are selected from the group consisting of 2,4-bis(1-aziridinylcarbonylamine)-toluene, bis(4-(1-aziridinylcarbonylamine)phenyl)methane, bis(3-chloro-4-(1-aziridinylcarbonylamine)-phenyl)methane, 2,2-bis(4-(1-aziridinlycarbonyloxy)-phenyl)propane, 1,4-bis(1-aziridinylcarbonyloxy)benzene, and 1,4-bis(1-aziridinylcarbonyl)benzene.

5. The thermosensitive recording material as claimed in claim 2, wherein the aromatic epoxy compounds for the colored image-stabilizing agent are selected from the group consisting of 4,4,-bis(2",3"-epoxypropyloxy)-diphenylsulfone, 2,2-bis(4'(2",3"-epoxypropyloxy)-phenyl)propane, 1,4-bis(2',3'-epoxypropyloxy)benzene, 4-(2'-methyl-2',3'-epoxypropyloxy)-4'-benzyloxy-diphenylsulfone, 4-(2",3"-epoxypropyloxy)-4'-(p-methyl-benzyloxy)diphenylsulfone, epoxidized o-novolak cresol resin, 4,4'-bis(2",3"-epoxypropyloxy)diphenylmethane, 4,4'-bis(2",3"-epoxypropylamino)diphenylmethane, bis(2",3"-epoxypropyl)4,4"-methylenedibenzoate, 4,4'-bis(2",3"-epoxypropyloxy)biphenyl, 4,4'-bis(2",3"-epoxypropyloxy)3,3',5,5'-tetramethylbiphenyl, 2,6-bis(2',3'-epoxypropyloxy)naphthalene, and bis(2,3-epoxypropyl)terephthalate.

6. The thermosensitive recording material as claimed in claim 1, wherein the compound of the formula (I) for the color developing agent is selected from the group consisting of N-(p-toluenesulfonyl)-N'-phenylurea, N-(p-toluenesulfonyl)-N'-(p-methoxyphenyl)urea, N-(p-toluenesulfonyl)-N'-(o-tolyl)urea, N-(p-toluenesulfonyl)-N'-(m-tolyl)urea, N-(p-toluenesulfonyl)-N'-(p-tolyl)urea, N-(p-toluenesulfonyl)-N'-(p-n-butylphenyl)urea, N-(p-toluenesulfonyl)-N',N'-diphenylurea, N-(p-toluenesulfonyl)-N'-(o-chlorophenyl)urea, N-(p-toluenesulfonyl)-N'-(m-chlorophenyl)urea, N-(p-toluenesulfonyl)-N'-(2,4-dichlorophenyl)urea, N-(p-toluenesulfonyl)-N'-methyl-N'-phenylurea, N-(p-toluenesulfonyl)-N'-benzylurea, N-(p-toluenesulfonyl)-N'-(1-naphthyl)urea, N-(p-toluenesulfonyl)-N'-(1-(2-methylnaphthyl))urea, N-(benzenesulfonyl)-N'-phenylurea, N-(p-chlorobenzenesulfonyl)-N'-phenylurea, N-(o-toluenesulfonyl)-N'-phenylurea, N-(p-toluenesulfonyl)-N'-methylurea, N-(p-toluenesulfonyl)-N'-ethylurea, N-(p-toluenesulfonyl)-N'-(2-phenoxyethyl)urea, N,N'-bis(p-toluenesulfonyl)urea, N-(p-toluenesulfonyl)-N'-phenylthiourea, N-(p-toluenesulfonyl)-N'-(o-diphenyl)urea, and N-(p-toluenesulfonyl)-N'-(p-ethoxycarbonylphenyl)urea.

7. The thermosensitive recording material as claimed in claim 1, wherein the compound of the formula (I) is present in an amount of 10 to 50% based on the total dry weight of the thermosensitive colored image-forming layer.

* * * * *